United States Patent [19]

Link

[11] 4,259,074
[45] Mar. 31, 1981

[54] METHOD FOR MAKING DENTURES
[75] Inventor: John A. Link, Scottsdale, Ariz.
[73] Assignee: TFT, Ltd., Scottsdale, Ariz.
[21] Appl. No.: 954,416
[22] Filed: Oct. 25, 1978
[51] Int. Cl.³ .............................................. A61C 9/00
[52] U.S. Cl. ...................................... 433/214; 433/37
[58] Field of Search ................... 32/2, 17; 433/37, 41, 433/213, 214, 171

[56] References Cited
U.S. PATENT DOCUMENTS 2,790,237  4/1957  Chaiken ................................. 32/2
3,464,111  9/1969  Gillard .................................... 32/2
4,097,992  7/1978  Hazar .................................. 433/171

Primary Examiner—Robert Peshock
Attorney, Agent, or Firm—Cahill, Sutton & Thomas

[57] ABSTRACT

The method incorporates the use of an impression tray having replicas of the artificial teeth to be used in the denture. A final impression is formed using the tray and a mold is formed from the tray; artificial teeth that are to be used in the denture are then inserted into the mold and the denture base material is then packed in the mold to form the dentures.

1 Claim, 2 Drawing Figures

METHOD FOR MAKING DENTURES

The present invention pertains to apparatus and methods for forming dentures, and particularly to novel apparatus and methods for significant reduction in time required for the formation of such dentures.

Prosthodontic techniques are specifically directed to the solution of problems encountered when replacing missing teeth by artificial devices such as dentures. In the manufacture of such dentures, it is critically important to insure precise fit and maintenance of proper dimensional relationships in the patient's mouth for the proper restoration of oral function. In addition to the functional relationships that must be maintained by the replacement of teeth with dentures, anatomical changes resulting from such tooth losses must be compensated to minimize changes in facial appearance. As a result of these requirements for properly fitting and functioning dentures, a close cooperative relationship is usually established between the dentist and the dental laboratory. The successive procedures that are used for the formation of and fitting of dentures can be very time consuming and expensive.

Attempts have been made to lessen the time and expense of dentures by providing pre-formed or ready made dentures that supposedly require only final fitting; such devices are seldom satisfactory. Present techniques for forming and fitting custom dentures usually require five appointments for the patient. Each appointment is followed by specific clinical and subsequent laboratory procedures in the formation of the dentures. Each of the steps is intended to insure compliance with all of the above-mentioned requirements for satisfactory dentures.

It is therefore an object of the present invention to provide a method and apparatus for making dentures that will reduce the time required and simplify the procedures necessary for the manufacture of the dentures.

It is another object of the present invention to provide a method and apparatus for the manufacture of dentures that would eliminate some of the previously required steps and patient appointments.

It is still another object of the present invention to provide a method and apparatus that will reduce the time required by the patient, the dentist, and the dental laboratory in the manufacture of dentures while nevertheless providing accurate fit of the dentures and proper oral function.

These and other objects of the present invention will become apparent to those skilled in the art as the description thereof proceeds.

The present invention may more readily be described by reference to the accompanying drawings in which.

Figure 1:
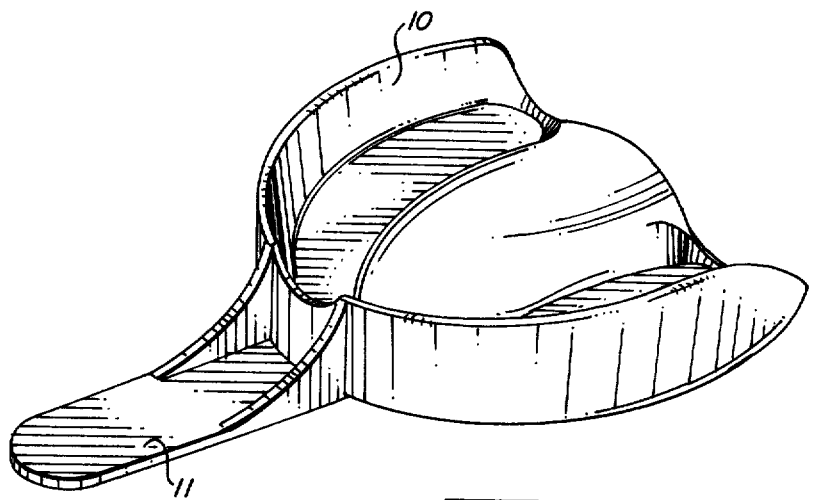
FIG. 1 is a perspective illustration of a prior art upper impression tray.

To facilitate understanding the method and apparatus of the present invention, the customary steps in the formation of custom dentures will now be described. The first step in the sequence of prosthodontic treatment is usually preceded by several preparatory appointments wherein the patient is prepared through appropriate procedures, surgical or otherwise, and the oral tissues are restored to optimal health. The first appointment then entails the formation of preliminary impressions by the dentist; these preliminary impressions are formed using a wax-like, alginate, rubber silicone, or other substance, manufactured for that particular purpose, that is placed in an impression tray. The tray and impression material is inserted into the patient's mouth and the material pressed and worked into the tissues to thereby form a negative of the patient's mouth. The preliminary impressions are immediately used to form a plaster or dental stone cast. These preliminary impressions and preliminary casts formed therefrom are not sufficiently accurate to form the basis for molding dentures; therefore, the preliminary casts are used as positive molds to form another impression tray called a custom tray. This custom tray will be smaller than the original tray and will more closely conform to the general configuration of the patient's mouth.

The first clinical and laboratory procedure having been completed, a second appointment with the patient is required wherein an impression material (usually of a finer and more accurately settable material) is placed in the custom tray and a secondary or final impression is made using impression material made for this purpose. The final impressions are used as molds to form master stone casts which are accurate negative reproductions of the final impression and form the basis upon which future denture construction will take place. The master casts are then used to support a wax-like moldable base plate which is hand formed onto the master cast. The base plate is the first rough approximation of the ultimate denture. A horseshoe shaped bead of wax called an occlusion rim is attached to the base plate along the area that will ultimately be occupied by artificial teeth. The occlusion rims, together with the base plate are used to obtain proper jaw relationships and are used for arranging the artificial teeth to be used in the denture.

The base plates and the occlusion rims thereon are then placed in the patient's mouth during a third appointment so that the rims can be trimmed to obtain proper vertical and centric relation and vertical dimension are recorded at this time; the size and shape of the specific teeth to be used in the denture are also determined at this time. Different mechanical devices may be used at this point in the procedure to record the jaw relationships. The base plates with occlusion rims are removed and are replaced on the master casts and mounted on articulator. The individual teeth are then set in the wax base and the bases are contoured.

The base plates with teeth are then trial fitted to the patient in a fourth appointment. The dentist will check for proper placement and appearance and will make whatever minor adjustments are necessary to insure proper jaw relationships. The finally adjusted wax bases and teeth are then used to form a mold; when the mold has sufficiently cured, the wax is melted and removed while the individual artificial teeth remain in the mold. The mold is then packed with resin denture base material and cured. The resin material fills the cavity of the mold and surrounds the upper portion of the artificial teeth remaining in the mold so that when the cured resin is removed from the mold, a rough finished denture is provided. The denture may then be finished by trimming and polishing techniques. The final appointment entails the delivery of the finished denture and the possible adjustments required to insure precise fit.

The usual procedure for inserting the denture base material in the mold is by a technique known as packing. The packing technique may be one of several available procedures wherein the resin is placed in the void provided in the mold. As used herein, the term "packing" is intended to include the various techniques such as injection molding or open packing. The resin may be any commercially available curable plastic material such as methyl methacrylate resin.

Figure 2:
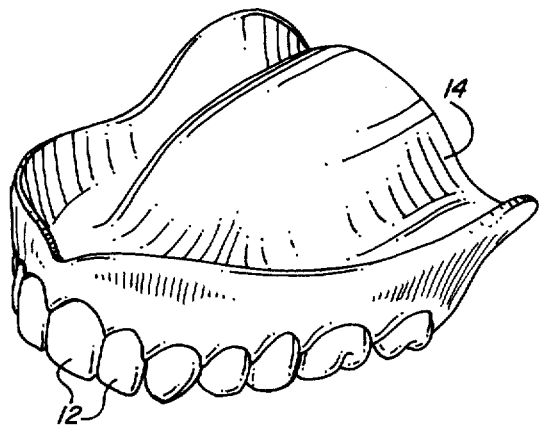
FIG. 2 is a perspective illustration of an upper impression tray constructed in accordance with the teachings of the present invention.

The above procedures begin with formation of a preliminary impression using an impression tray. A typical prior art upper impression tray is shown in FIG. 1 wherein it may be seen that a channel 10 for the receipt of impression material is provided while a handle 11 may be molded directly in the tray to facilitate insertion of the tray into the patient's mouth. A similar impression tray is provided for forming lower impressions. It is important to note that such impression trays are usually large and are intended to provide a support for impression material only to the extent necessary to form a preliminary impression. It will be remembered that the preliminary impressions, and the subsequent preliminary casts, are then used to form secondary or custom trays. In contrast to impression trays of the prior art, the apparatus of the present invention as shown in FIG. 2 forms an upper impression tray that generally conforms to the appearance of a finished denture; a lower impression tray is used to form a set. However, the apparatus of FIG. 2, as well as lower impression trays, are provided in a range of sizes; further, it must also be remembered that the impression tray formed by the device of FIG. 2 replaces not only the impression tray such as shown in FIG. 1, but also replaces the second or custom tray heretofore necessitated by prior art techniques. It is important to note that the device of FIG. 2 incorporates replicas 12 of the artificial teeth that are ultimately to be used in the denture. The replicas 12 are formed and molded integrally with the impression tray 14. The device is formed from any suitable moldable plastic material such as acrylic plastic. It is of substantial importance that the resulting molded device incorporates replicas 12 that are identical to the artificial teeth that are to be used in the denture. A wide variety of standard sizes, shapes, and colors of artificial teeth are available and the replicas 12 must be formed to the same size and shape as the chosen artificial teeth for reasons now to be explained.

The method of the present invention may now be described. In the method of the present invention, the apparatus of FIG. 2 is utilized as a custom impression tray; impression material for taking a final impression is placed in the tray and the tray inserted into the patient's mouth during the first patient visit. A similar impression tray is provided for making the lower dentures. Since the teeth (i.e., replicas thereof) are already in place, the proper occlusion plane, the centric relation and the vertical dimension can accurately be determined during the first appointment. The apparatus of FIG. 2, having the final impression therein, is removed from the patient's mouth and is used as the pattern for the formation of a mold. The pattern is invested in the same manner as the wax bases and artificial teeth of the prior art method. When the investment material used for making the mold cures, the apparatus of FIG. 2 is removed. At this point of the method, it will be noted that a mold has been made that conforms to the same mold that would have been made by the prior art process (but only after the fourth appointment) with the exception that the mold made by the new method does not contain the artificial teeth that are to be used in the denture; rather, precise negative impressions of the artificial teeth are formed in the mold by the replica teeth integrally formed in the impression tray of FIG. 2. Therefore, at this point in the process, the chosen artificial teeth are individually inserted into the appropriate spaces provided therefore in the mold and the denture base material is packed in the mold and processed or cured to form the complete denture.

The procedure to be followed by the dentist using the apparatus and method of the present invention therefore becomes considerably simplified. Assuming that a full set of dentures are to be manufactured, the dentist would normally place the upper tray of the present invention into the patient's mouth and trim and adjust the tray; small amounts of wax may be placed on the tissue side of the tray to obtain the precise positioning of the tray. Impression material may then be placed in the tray to make the final impression. With the upper tray in position, the lower tray may then be inserted and trimmed and adjusted having the patient close in centric to a predetermined vertical. Adjustments may be made by grinding on the tissue side of the tray or adding stops as necessary for proper alignment. Using appropriate impression material, the final impression is then made with the lower tray. The upper and lower trays now form complete patterns for the production of a full set of dentures. To limit distortion of the final impressions and to preserve the close fit of the impression material, stone casts can be made immediately following the fitting. If a very thin palate is desired, the palate area of the tray may be removed and replaced with the wax while the tray is mounted on the stone cast. The wax may then be thinned to the desired thickness.

By using the apparatus and method of the present invention, a substantial proportion of the total time required for the production of dentures is eliminated; further, the time savings are distributed between the clinical and laboratory procedures. Therefore, the time consumed by the dentist and the laboratory are reduced resulting in a cost reduction to the patient; significantly, the time between the initial impression and the delivery of the finished denture (which time period is a period of embarrassment to the patient) is substantially reduced.

I claim:

1. A method for making dentures with artificial teeth, said method comprising the steps of:
    (a) forming an impression with impression material supported on an impression tray which tray includes replicas of the artificial teeth that are to become a part of the dentures;
    (b) inserting the impression tray and supported impression material in investment material;
    (c) curing the investment material to form a mold;
    (d) removing the impression tray and impression material from the mold to leave a cavity duplicative of the impression tray and impression defined by the supported impression material;
    (e) individually inserting artificial teeth corresponding to the replicas of artificial teeth defined by the impression tray in the parts of the mold cavity formed by the replicas of the artificial teeth;
    (f) packing the remaining part of the mold cavity with denture base material; and
    (g) curing the denture base material to form the denture with artificial teeth embedded in the denture base material.

* * * * *